United States Patent [19]

Rosenbluth et al.

[11] Patent Number: 5,030,227
[45] Date of Patent: Jul. 9, 1991

[54] BALLOON DILATION CATHETER

[75] Inventors: Robert F. Rosenbluth; Jay A. Lenker, both of Laguna Beach; George R. Greene, Costa Mesa; Barry M. Calvarese, Cardiff, all of Calif.

[73] Assignee: Advanced Surgical Intervention, Inc., San Clemente, Calif.

[21] Appl. No.: 360,088

[22] Filed: Jun. 1, 1989

Related U.S. Application Data

[63] Continuation-in-part of Ser. No. 201,686, June 2, 1988 Pending.

[51] Int. Cl.$^5$ ............................................. A61M 29/02
[52] U.S. Cl. ...................................... 606/192; 604/96; 604/104; 604/170; 128/4; 128/662.06
[58] Field of Search .................................. 604/96–102, 604/164, 170, 8, 280, 104; 606/192–194; 128/660.01, 660.07, 4, 662.06

[56] References Cited

U.S. PATENT DOCUMENTS

| | | |
|---|---|---|
| 550,238 | 11/1895 | Allen, Jr. . |
| 2,936,760 | 5/1960 | Gants . |
| 3,045,677 | 7/1962 | Wallace . |
| 3,720,199 | 3/1973 | Rishton et al. . |
| 3,822,702 | 7/1974 | Bolduc et al. ........................ 604/96 |
| 3,835,842 | 9/1974 | Iglesias . |
| 3,848,602 | 11/1974 | Gutnick . |
| 3,977,408 | 8/1976 | MacKew . |
| 4,432,757 | 2/1984 | Davis, Jr. . |
| 4,439,186 | 3/1984 | Kuhl ..................................... 604/99 |
| 4,445,892 | 5/1984 | Hussein et al. ......................... 128/4 |
| 4,461,280 | 7/1984 | Baumgartner . |
| 4,561,446 | 12/1985 | Hetz . |
| 4,636,346 | 1/1987 | Gold et al. . |
| 4,660,560 | 4/1987 | Klein . |
| 4,697,595 | 10/1987 | Breyer et al. ................... 128/662.06 |
| 4,733,652 | 3/1988 | Kantrowitz et al. . |
| 4,744,366 | 5/1988 | Jang . |
| 4,762,128 | 8/1988 | Rosenbluth . |
| 4,763,654 | 8/1988 | Jang . |

OTHER PUBLICATIONS

Karl-Axel Backman, Dilatation of the Prostate According to Diesting, pp. 266–274.
V. Aalkjaer, Transurethral Resection/Prostatectomy Versus Dilatation Treatment in Hypertrophy of the Prostate II (1965) pp. 17–22.
K. J. Oravisto, Indications for Deisting's Prostatic Dilatation in the Treatment of Prostatic Dypertrophy, pp. 202–206.
Werner Deisting, Transurethral Dilatation of the Prostate, 1956, pp. 158–171.
510K Premarket Notification ASI Urethral Di Lation Catheter.

Primary Examiner—Stephen C. Pellegrino
Attorney, Agent, or Firm—Knobbe, Martens, Olson & Bear

[57] ABSTRACT

Disclosed is an apparatus and method for the treatment of the symptoms of obstructive prostatism. The apparatus comprises an expandable dilation catheter and preferably an axially elongate sheath, adapted for transurethral insertion via the external opening of the urethra. The sheath is ellipsoid in cross-section, and provides an initial path through which the catheter and a standard cystoscope lens is guided. The dilation catheter or the sheath are provided with a non-radiological locating means for positioning the dilation portion of the catheter with respect to an anatomical landmark. Once the catheter has been properly positioned with respect to both the bladder neck and the sphincter, the dilation balloon may be inflated to force open the affected prostatic urethra and eliminate the obstruction.

16 Claims, 6 Drawing Sheets

BALLOON DILATION CATHETER

BACKGROUND OF THE INVENTION

This is a Continuation-In-Part of parent patent application Ser. No. 201,686; filed June 2, 1988; inventors Robert F. Rosenbluth, Jay Alan Lenker, and George Robert Greene; entitled Balloon Dilation Catheter.

The present invention relates generally to the field of catheters. More specifically, the present invention relates to catheters which are adapted to be inserted into the urethral lumen to alleviate obstructive prostatism, a condition quite common in males over the age of 50.

The prostate is a somewhat pear-shaped gland that extends around the urethral lumen from the neck of the bladder to the pelvic floor. Because of the close relationship of the prostate to the urethra, enlargement of the prostate, usually referred to as hypertrophy or hyperplasia, may fairly quickly obstruct the urethra, particularly if the hyperplasia occurs close to the lumen. Such an obstruction inhibits normal micturition, which causes an accumulation of urine in the bladder.

The surgical treatment of hyperplasia of the prostate gland has been a routine procedure in the operating room for many years. One method of surgical treatment is open prostatectomy whereby an incision is made to expose the enlarged prostate gland and remove the hypertrophied tissue under direct vision. Another method of treating obstructive prostatism is a technique known as transurethral resection. In this procedure, an instrument called a resectoscope is placed into the external opening of the urethra and an electrosurgical loop is used to carve away sections of the prostate gland from within the prostatic urethra under endoscopic vision.

The technique of transurethral resection offers many benefits to the patient as compared to open prostatectomy. Using this technique, the trained urologist can remove the hypertrophied prostate with less patient discomfort, a shorter hospital stay and lower rates of mortality and morbidity. Over 333,000 patients underwent this procedure in the U.S. in 1985, with an average hospital stay of six days. Notwithstanding the significant improvement in patient care resulting from the widespread application of transurethral resection, there remains a need for a less invasive method of treating the symptoms of prostate disease.

One of the earliest methods of relieving acute urinary retention, a symptom associated with prostate disease, was the placement of a catheter through the external urethral opening into the bladder, thereby allowing the outflow of urine from the bladder by way of the catheter lumen. These urinary catheters typically employ a balloon at the tip which, when inflated, prevents the expulsion of the catheter from the body. However, due to problems of infection, interference with sexual activity, and maintenance involved with such catheters, they are generally unacceptable for long term treatment of micturition problems.

U.S. Pat. No. 4,432,757 to Davis, Jr. teaches the use of an indwelling urethral catheter assembly, having a Foley-type balloon disposed near the distal end thereof and a substantially non-compliant balloon lead shaft proximate to the Foley-type balloon. The device is adapted to be inserted through the urethra up into the bladder. The Foley-type balloon and the balloon lead shaft are then inflated, although the balloon lead shaft remains relatively non-compliant and therefore does not expand appreciably. Gentle traction is then applied to a catheter sleeve head to sever the sleeve from the remainder of the catheter, leaving the balloon lead shaft in position within the urethra.

Another method of treating hypertrophy of the prostate gland without the need for surgery has been to inject medications into the prostate gland by means of a catheter. Such a device is disclosed in U.S. Pat. No. 550,238 to Allen, wherein two balloons are disposed along two sections of a catheter, and inflated to isolate an area within the urethra prior to the injection of the medication. However, these injections are frequently ineffective as the prostate gland exhibits only a limited ability to absorb the injected antibiotics, and proper positioning and retaining of the catheter with respect to the affected area is extremely difficult.

A substantial improvement in an apparatus and corresponding method of treatment for obstructive prostatic hypertrophy is disclosed in Klein, U.S. Pat. No. 4,660,560. In Klein's method, a calibrating catheter is used to measure the distance between the neck of the bladder and the bottom of the prostate gland. A dilation catheter, having an annular balloon with a length equivalent to the measured length, and a Foley-type balloon at the distal end thereof is then inserted into the urethra until the Foley-type balloon is within the bladder. The Foley balloon is then inflated in the bladder and is used to position the dilation balloon in the prostrate. The latter balloon is then inflated, to force the prostate away from the urethral lumen. Use of the Klein catheter can effectively eliminate uncertainty regarding positioning of the upper (distal) end of the dilation balloon, thereby significantly facilitating the treatment of prostatic hypertrophy.

In practicing the Klein method, after the calibration catheter is used to measure the length of the affected prostate, it is withdrawn from the urethra, and the dilation catheter is then inserted. Proper insertion of the dilation catheter is crucial, as stretching of the external urethral sphincter muscle, which lies just below the prostate, could cause incontinence. Although some means of visualizing placement of the proximal end of the dilation balloon is therefore desirable, the catheter is too large to fit through a conventional cystoscope sheath. Moreover, bleeding, which is common during such a procedure, not infrequently obscures the field of view of a cystoscope lens, making it useless.

Accordingly, in practicing the method of the Klein patent, there is a need for a method and apparatus to permit effective and sure positioning of the proximal end of the dilation balloon with respect to the external urethral sphincter. There is a particular need to permit visualization of the balloon placement in vivo during the course of the surgical procedure.

SUMMARY OF THE INVENTION

Briefly, the present invention provides a dilation catheter and sheath of novel design for use as a non-surgical alternative to the treatment of the symptoms of obstructive prostatism.

In accordance with one aspect of the present invention, there is provided an intraurethral dilation device for relieving the symptoms of obstructive prostatism which is adapted for easy insertion into the urethra for pressure dilation of the prostate, so as to force the prostate away from the urethral lumen and thereby eliminate the obstruction. The dilation device is further provided in one embodiment with an introduction sheath, suitable for housing a cystoscope lens or other locating means, and a dilation catheter. Preferably, the dilation catheter is provided with an expandable locating balloon, disposed near the distal tip of the catheter which, when inflated within the bladder, will provide an anchor with the bladder neck. At least one dilation balloon is preferably provided on the catheter, proximate the locating balloon which, when inflated, conforms to a preselected configuration, so as to radially outwardly dilate the obstruction away from the urethral lumen.

In accordance with a further embodiment of the present invention, there is provided an intraluminal dilation apparatus having non-radiological means thereon for locating the position of a dilation means within a body lumen, with respect to an anatomical landmark. The apparatus comprises an elongate catheter, having a means for dilation of the body lumen carried thereon. Preferably, the dilation means is an inflatable balloon, and, in an alternative embodiment, the dilation means comprises two or more axially adjacent, independently controlled dilation balloons. The apparatus further comprises a locating means associated with the dilation catheter for locating the dilation means with respect to the anatomical landmark. Preferred locating means include a standard cystoscope, an ultrasound transducer, a muscle contractility detector or an electromylogram pick-up.

There is additionally provided a method of treating the systems of obstructive prostatism by dilation of the prostatic urethra, comprising the steps of inserting a dilation means into the urethra, the dilation means having a non-radiological locating means for positioning the dilation means relative to an anatomical landmark. The location of the dilation means within the urethra is adjusted with respect to the anatomical landmark using the non-radiological locating means, and the dilation means is thereafter expanded so as to radially outwardly dilate the prostatic urethra.

Further objects, features and other advantages of the present invention will become apparent from the ensuing detailed description, considered together with the appended drawings.

DETAILED DESCRIPTION OF THE PREFERRED EMBODIMENT

Figure 1:
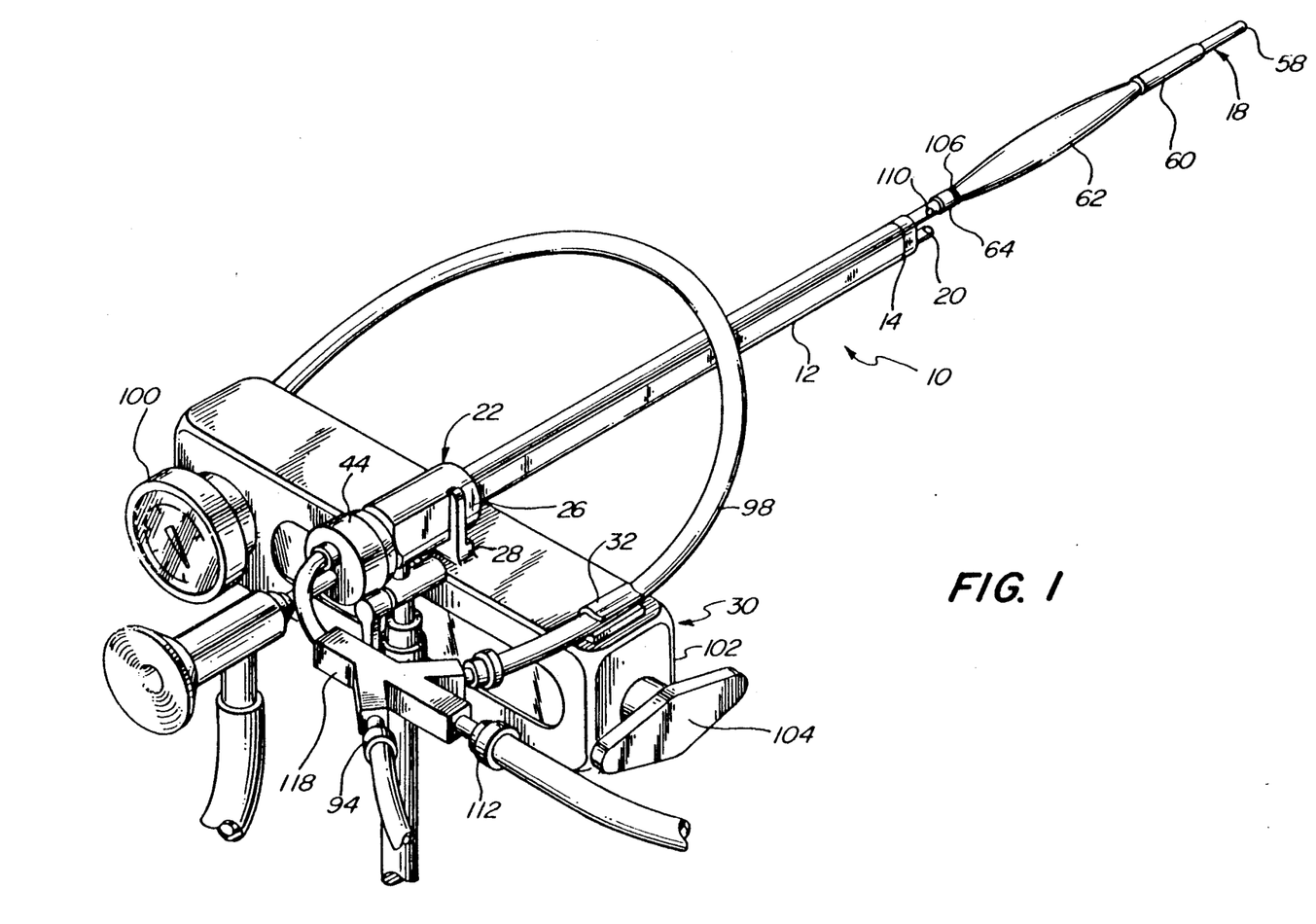
FIG. 1 is a perspective view of a dilation catheter and sheath assembly in accordance with one embodiment of the present invention.

Referring now to the drawings in detail, wherein like reference numerals designate like elements throughout the several views thereof, there is shown generally at 10 in FIG. 1, a dilation catheter and sheath assembly embodying the present invention in a preferred form. The sheath 12 is advantageously a substantially rigid, axially elongate hollow shaft throughout most of its length, but having a flexible distal tip 14. The sheath 12 exhibits an inner surface 16 which is substantially ellipsoid in cross-section, and is adapted to receive and guide an axially elongate catheter 18 and an endoscope 20 longitudinally therethrough. Advantageously, the particular endoscope used is known as a cystoscope. Alternatively, a variety of other means for locating anatomical landmarks within the body lumen may be used, as discussed infra.

Figure 2:
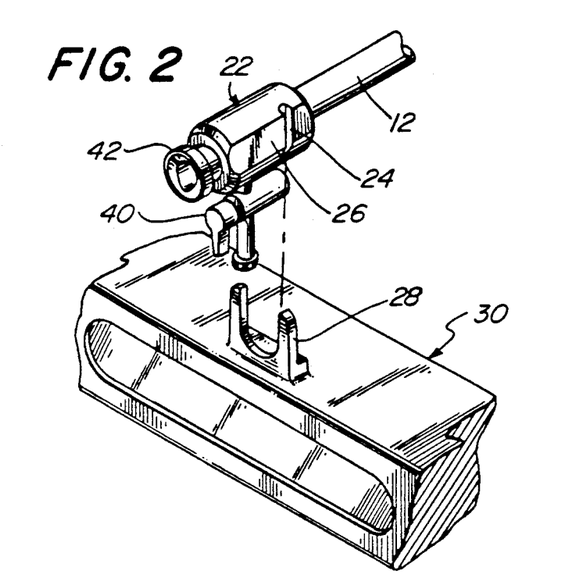
FIG. 2 is a partial assembly view of the clipping mechanism.
Figures 4, 5, 6:
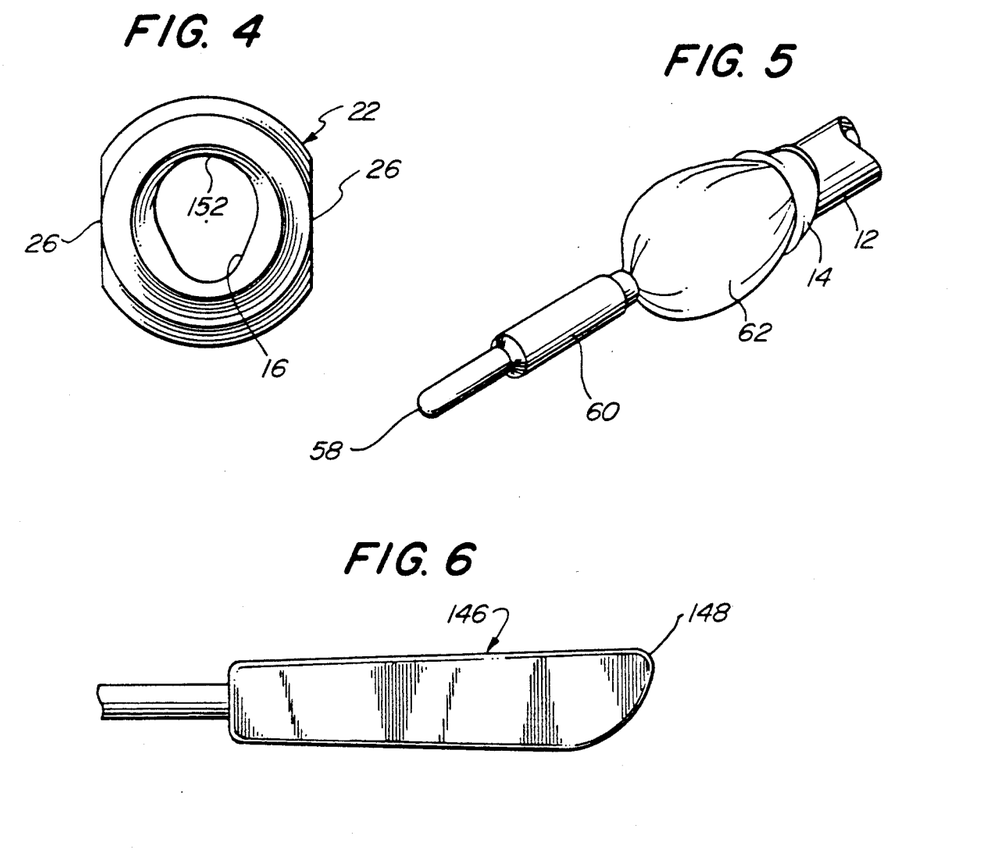
FIG. 4 is an end view of the sheath, showing the unique ellipsoid shape of the inner walls thereof.
FIG. 5 is a perspective view of the tip of the sheath, as being deformed by a once-inflated dilation balloon, so as to guide the balloon into the sheath before removal from the urethral lumen.
FIG. 6 is a side view of the tip of an obturator.

In one embodiment of the invention, a cylindrical housing 22, disposed near the base of the sheath, exhibits a pair of grooves 24, formed upon two flattened surfaces 26 of the cylindrical housing 22, on opposite sides thereof. An end view of the cylindrical housing 22, as shown in FIG. 4, illustrates the ellipsoid shape of the inner walls 15 of the sheath 12, and the flattened side surfaces 26 thereof. A U-shaped clip 28 is integrally connected to the top of an inflation device 30 and is adapted to removably receive and retain the cylindrical housing 22 so as to enable the device 10 to be operated by one person, without the need for assistance. The removable attachment of the sheath 12 to the U-shaped clip 28 is illustrated in FIG. 2. A C-shaped clip 32 may also be provided on the body of the inflation device 30, to removably receive and retain the catheter 18 therein and provide additional support for the proximal end of the device, thus controlling the catheter so it does not interfere with the eyepiece of the endoscope.

Situated on the underside 36 of the cylindrical housing 22 is a drainage port 38, having a cock valve 40 secured therein. The cock valve 40 is adapted to allow back-flowing fluids to escape the sheath 12 when positioned in the "on" position, and to prohibit the release of such fluids when in the "off" position.

Figure 3:
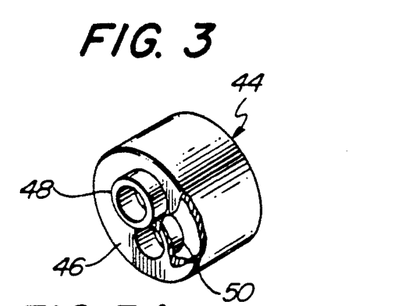
FIG. 3 is a perspective view of a septum, showing an inwardly extending boot sleeve in cut away.
Figure 3A:
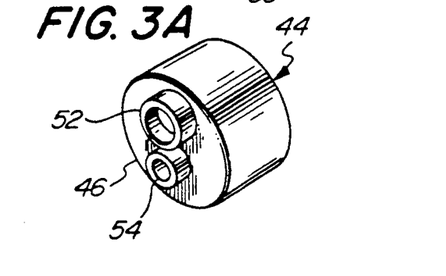
FIG. 3a is a perspective view of a second type of septum, having both boot sleeves projecting outwardly.

The cylindrical housing 22 includes a hub portion 42, disposed at the proximal end thereof. A rubberized septum 44, preferably formed from a silicon rubber compound, is detachably placed onto the hub 42 of the cylindrical housing 22 so as to provide a seal therefor. As best seen in FIGS. 3 and 3a, the septum 44 is a circular cap 46, having a pair of boot sleeves 48, 50 integrally connected to the proximal end of the cap 46. In one embodiment, the septum 44 exhibits an outwardly extending boot sleeve 48 an inwardly extending boot sleeve 50. The boot sleeves 48, 50 are adapted to receive the cystoscope lens 20 and the dilation catheter 18, and provide the septum 44 with elasticity at the point of contact therebetween. Without the presence of such sleeves, the rubberized septum 44 would itself deform if a force were applied to either the catheter 18 or cystoscope lens 20, thereby detracting from the septum's sealing ability Further, the boot sleeves 48, 50 are adapted to readily adjust to and grip the outer diameter of the catheter 18 and lens 20 to yield a good seal therebetween. In an alternative embodiment, as shown in FIG. 3a, both of the boot sleeves 52, 54 extend outwardly from the septum cap 44. This embodiment is possible only when there exists sufficient room on the outside of the septum, such that a sharing of a common wall between the two sleeves is not necessitated.

Figures 11, 12, 13, 14:
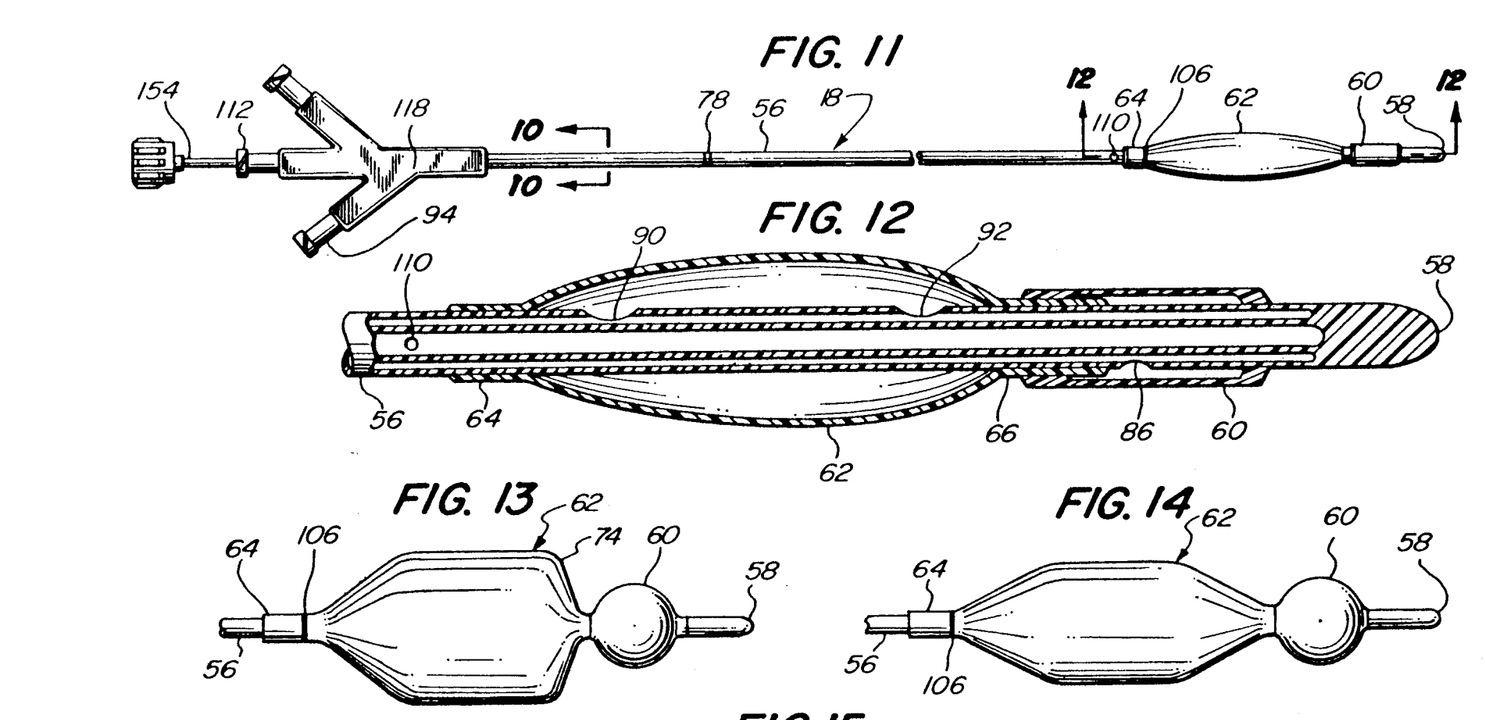
FIG. 11 is a side view of a dilation catheter, having a stylet removably inserted therein.
FIG. 12 is a cross-sectional view, taken along line 12—12 of FIG. 11, showing the overlap of the shoulder of the locating balloon with the shoulder of the dilation balloon.
FIG. 13 is a side view of a dilation balloon, in an inflated state, exhibiting a squared-off configuration at one end, and a tapered configuration at the opposite end thereof, in accordance with one embodiment of the present invention.
FIG. 14 is a side view of a dilation balloon, having both ends in a tapered configuration, in accordance with an alternative embodiment of the present invention.

As best seen in FIG. 11, the dilation catheter 18 of the present invention comprises an axially elongate catheter shaft 56, having a tapered guiding end 58, and a plurality of parallel conduits disposed therein. Situated near the guiding end 58 of the catheter shaft 56 is a locating balloon 60. The locating balloon 60 is a small latex Foley-type balloon, adapted for inflation by a source of pressurized fluid. Adjacent the locating balloon 60 is a larger dilation balloon 62, having a proximal shoulder 64 and a distal shoulder 66.

A feature of this invention is that the distal shoulder 66 of the dilation balloon 62 is overlapped by a portion of the locating balloon 60, such that, when the balloons are expanded, a minimal valley is left between the two balloons. Both of the balloons 60, 62 are bonded to the outer perimeter of the catheter shaft 56 by suitable adhesive or thermal process. In a similar manner, more than one axially adjacent dilation balloons can be provided on the dilation catheter, each provided with a unique inflation lumen extending through the catheter to a selectively controllable pressure source. The use of two or three or more dilation balloons permits control over the effective length of the dilation region of the catheter, as will be understood by one of skill in the art.

Figure 17:
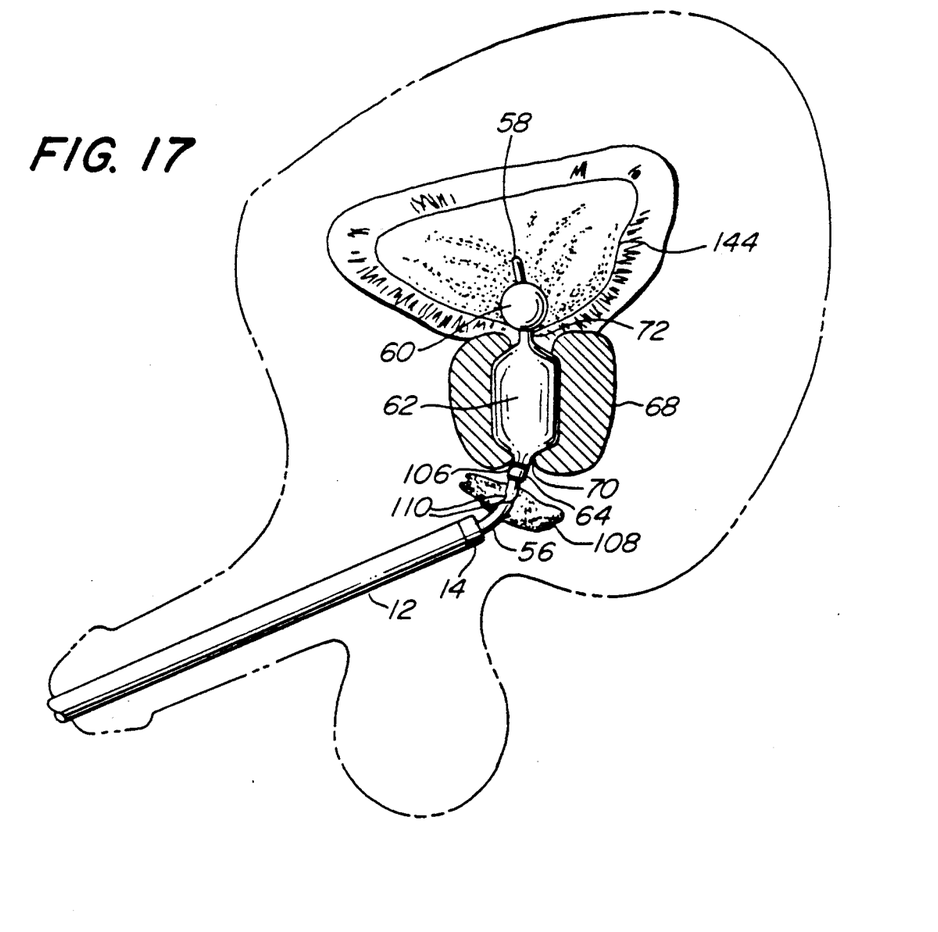
FIG. 17 is a cross-sectional view of the urethral dilation catheter of the present invention operatively inserted within the male urinary tract.

While the overlap of the locating balloon 60 onto the shoulder 66 of the dilation balloon 62 increases the area of dilation by minimizing the distance between the locating balloon 60 and the dilation balloon 62, suboptimal dilation of the affected prostatic urethra 68 still exists due to the tapered nature of expandable balloons, commonly used in dilation processes. To achieve optimal dilation near the ends 70, 72 of the affected prostatic urethra 68, the dilation balloon 62 can be molded with a steep, squared off end 74, as illustrated in FIG. 13. Depending on the nature of the affected area of the prostatic urethra 68, it may be desirable to enable urethral dilation very close to the bladder neck 72 or the external sphincter muscle 70. Accordingly, either end of the dilation balloon 62, neither end, or both ends may be provided with a substantially vertical configuration as illustrated in FIGS. 13, 14 and 17.

A material which is well adapted to construction of the dilation balloon 62 of the present invention is polyethylene terephthalate (PET), such as KODAK's 9921. Preferably, the balloon 62 is extruded in a straight pipe configuration and then stretched and blown under high temperature and pressure to yield the desired shape 74. This type of technique is commonly applied in the making of angioplasty balloons. It should be noted that the PET material used to construct the dilation balloon exhibits superior tensile strength characteristics to that of materials used in manufacturing other types of dilation balloons, for example older angioplasty balloons. The PET material used to construct the dilation balloon of the present invention has a tensile strength of between 20,000 to 50,000 psi, and is rated to withstand at least 3 atmospheres of pressure, and as much as 5 atm.

If a rubberized latex material were used to fabricate the dilation balloon of the present invention, the walls of the balloon would necessarily be much thicker in order to withstand the exceedingly high pressures required for adequate dilation of the affected prostatic urethra. Thus, the PET material, by virtue of its superior strength, allows a thinner balloon to be utilized. The thinness of the balloon thus formed, makes possible a dilation balloon 62 which, in an uninflated state, conforms to the external walls of the catheter shaft 56, thereby providing a dilation catheter 18 having substantially the same size and shape as the unstretched lumen. However, the increased strength of the material also dictates a balloon which is somewhat stiff and substantially less pliable than a latex balloon.

Consequently, when negative pressure is applied to collapse the dilation balloon 62 made of the PET material, sharp ridges may form on the exterior surface thereof. Advantageously, the distal tip 14 of the introduction sheath 12 is formed of a flexible material, which readily deforms to the gross contours of the deflated dilation balloon 62, so as to coerce the balloon 62 into the introduction sheath 12 prior to the withdrawal of the catheter 18 from the urethra. Preferably, the tip 14 is formed from a substantially malleable Poly Vinyl Chloride (PVC) compound, which is RF welded to rigid shaft portion 12 of the sheath.

To ensure that the catheter 18 is fully within the introduction sheath 12 prior to the withdrawal thereof, visual indicia, such as the marking 78 on the exterior shaft 56 of the catheter 18 is provided. As the catheter shaft 56 and deflated dilation balloon 62 are gradually withdrawn from the urethra, the indicia 78 will be advanced out of the sheath 12. When the designated indicia 78 becomes visible, the catheter 18 is fully retracted within the sheath 12, and the device 10 may be withdrawn, without causing undue trauma to the urethral lumen.

Figure 10:
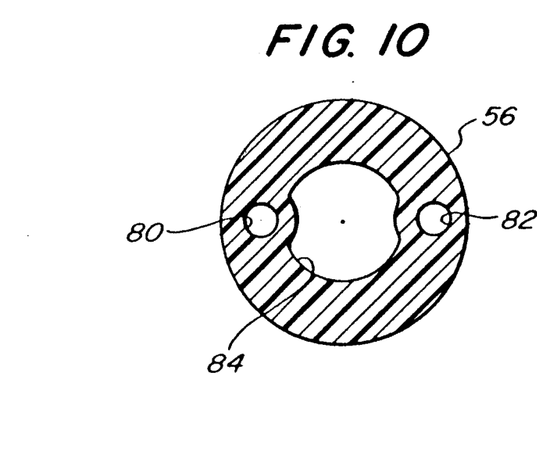
FIG. 10 is a cross-sectional view, taken along line 10—10 of FIG. 11, showing the lumen arrangement within the catheter shaft.

As best seen in cross-section in FIG. 10, the catheter shaft 56 houses a pair of circular inflation conduits 80, 82 and an irrigation conduit 84. The inflation conduit 80 having an aperture 86 underlying the locating balloon 60 exhibits a tubular passageway which permits pressurized fluid to be transmitted into the chamber enclosed by the locating balloon 60 so as to selectively inflate the balloon 60 to a suitable level. Likewise, the inflation conduit 82 having a pair of inflation apertures 90, 92 underlying the dilation balloon 62 allows pressurized fluid to selectively fill the balloon 62 to a desired level.

To facilitate inflation of the locating balloon 60, a simple fluid valve 94 may be connected to the proximal end of the conduit 80. This valve 94 is integrally connected to the inflation conduit 80 and may be easily manipulated to allow quick sealing of the conduit 80 and maintain the pressurized fluid within the balloon chamber 60 and the conduit 80. The locating balloon 60 may be pressurized by inserting a hypodermic syringe (not shown) into the valve 94, with the valve 94 in its open condition. By forcing fluid into the conduit 80, the locating balloon 60, at the distal end of the inflation conduit will be inflated. The valve 94 may then be closed, and the hypodermic syringe removed, leaving the locating balloon 60 in an inflated state.

Since inflation of the dilation balloon 62 is more critical, the source of pressurized fluid 98 used to inflate the dilation balloon 62 is connected to a pressure gauge 100. Preferably, the inflation device 98 includes a syringe barrel 102 having a threaded rod and ratchet mechanism 104 which replaces the conventional plunger. This configuration allows fine tuning of the pressure amassed within the dilation balloon 62 by screw turning the threaded rod 104. It has been determined that an intraballoon pressure of approximately 3 atm., or 45 p.s.i.g. is sufficient to force the prostate away from the urethral lumen to relieve the obstruction and reestablish normal micturition.

As a further alternative, the dilation catheter of the present invention can be configured to carry an expandable implantable stent over the dilation region thereof. This embodiment of the present invention would permit both expansion of the urethra and leaving behind of an expanded intraluminal support to ensure long-term patency of the urethra. The use of such implantable stents is disclosed in detail in U.S. Pat. No. 4,762,128 issued to Robert F. Rosenbluth on Aug. 9, 1988, the disclosure of which is hereby incorporated by reference in the present case.

The catheter comprises a radially expandable region near the distal end thereof which, in its unexpanded state, has an outer diameter that is preferably slightly smaller than the outer diameter of the adjacent region of the catheter. Thus, the collapsed expandable region forms the bottom of an annular depression about the catheter.

The stent is removably, coaxially disposed about the expandable region of the catheter and within the annular depression formed therearound, and is controllably radially outwardly expandable in response to pressure from the expandable region of the catheter. When the stent is coaxially disposed about the expandable region of the catheter, and in an unexpanded state, the outer diameter of the unexpanded stent is approximately the same as or less than the outer diameter of the adjacent region of the catheter. Preferably, the distal end of the catheter comprises a flexible, resilient material in a shape to facilitate insertion into and negotiation of a collapsed lumen with minimal trauma to the lining thereof. Alternatively, for use with an introduction sheath, the stent may extend radially outwardly of the adjacent catheter shaft in the unexpanded state.

The radially outwardly expandable tubular stent for restoring patency to a collapsed portion of the urethral lumen comprises a material that is compatible with the urethral environment, and is capable of remaining in its expanded state following removal of the expansion catheter described above, thereby holding open the lumen of the urethra against a restricting pressure, such as that exerted by a hypertrophied prostate gland. The cross section of the expanded stent may be circular, or may also be a non-circular configuration which more closely corresponds to the shape of the normal lumen within the urethra. One embodiment of the stent in its expanded state comprises a substantially uniform cross-sectional area throughout its axial length. In another embodiment, the stent comprises a smaller cross-sectional area at its axial ends than in the central region thereof. In addition, the axial end regions of the stent may comprise a flexible material, or may taper in a radial inward direction thereby easing the transition from the lumen of the stent to the lumen of the urethra.

Figure 16:
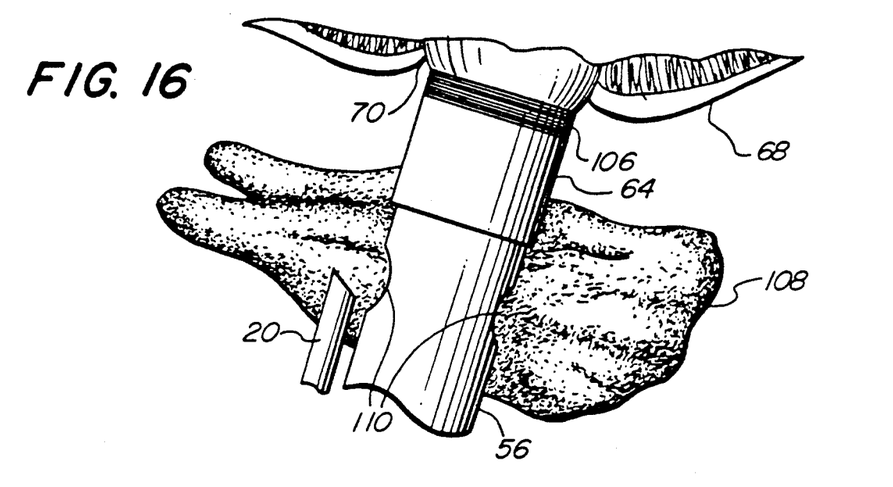
FIG. 16 is a magnified view of the marking disposed near the proximal end of the dilation balloon showing clearance of the external sphincter muscle.

Referring to FIGS. 11 and 16, near the proximal end of the dilation balloon 62, and encircling the proximal shoulder 64 thereof, is a heavy black line 106 for use with the cystoscope embodiment of the present invention. Prior to inflating the dilation balloon 62, care should be taken to ensure that the black line 106 does not extend onto any portion of the external urethral sphincter muscle 108. This is vitally important as accidental dilation of the sphincter 108 may cause the patient to lose voluntary control over micturition, especially if the sphincter experiences plastic deformation, i.e., the inability to return to its original shape.

An important feature of this invention is the provision of an irrigation system. As described below, the system provides the dual features of both flushing blood away from the lens of the cystoscope to aid in the viewing of the external sphincter muscle and the black line 106 on the shoulder 64 of the dilation balloon 62 and inhibiting coagulation of blood within the urethra. This flushing system includes a plurality of irrigation ports 110 disposed along the exterior shaft 56 of the catheter 18, proximate to the line 106 are provided. The irrigation ports 110 are adapted to continuously flush fluid, for example, saline, from the irrigation conduit 84, which extends through the center of the catheter shaft 56. The irrigation conduit 84 is provided with a coupling device 112 at the proximal end thereof, adapted to receive a source of flushing fluid, which, for example, can be a hanging container of saline (not shown), having a length of flexible tubing extending therefrom, for connection to the coupling device 112. The source of fluid is elevated and allowed to flow by gravity through the irrigation conduit 84 and out the irrigation ports 110, so as to flush blood away from the lens 20 and allow the urologist an unobstructed view of the external sphincter muscle 108 and the line 106 encircling the proximal shoulder 64 of the dilation balloon 62.

In addition to permitting an unobstructed view of the proximal shoulder 64 of the balloon 62, the flushing of blood inhibits coagulation, and therefore substantially eliminates clotting within the urethral lumen. Backflowing flushing fluid and blood is drained from the urethra through introduction sheath 12 by gravity flow. A drainage reservoir (not shown) is connected to the cock valve 40 which, when in its open position, allows the backflowing fluids to drain, by gravity flow, into the reservoir and subsequently disposed of. Alternatively, the flushing fluid can be supplied through the sheath 12 to flush blood away from the cystoscope lens 20. In this embodiment, the irrigation ports 110 of the irrigation conduit 84 function as influent ports to drain the flushing fluid and blood out of the urethra.

Figure 9:
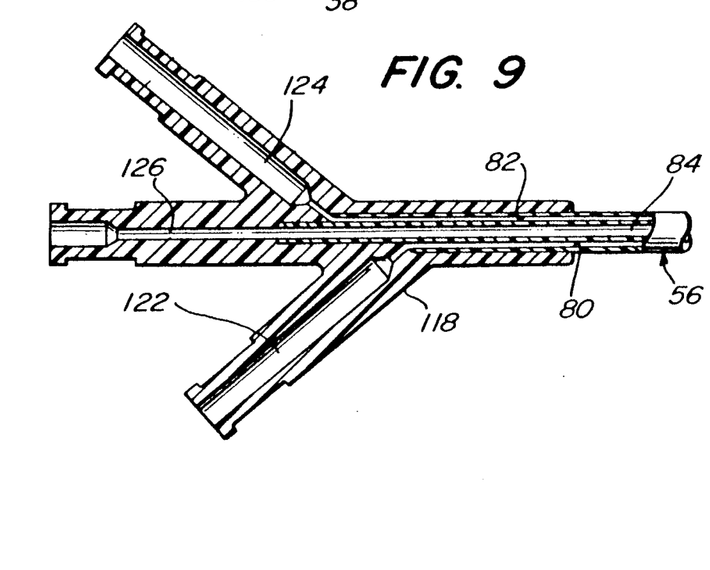
FIG. 9 is a cross-sectional view, illustrating a plastic manifold disposed at the proximal end of the dilation catheter during the molding process.

Located at the proximal end of the catheter shaft 56, and integrally connected thereto, is a Y-shaped plastic manifold 118. The manifold 118 is adapted to define and separate the trio of conduits 80, 82, 84 disposed within the body of the catheter shaft 56. Preferably, the manifold 118 is preformed in the Y-shaped configuration and is adapted to connect to the catheter shaft 56 and trio of conduits at the proximal end thereof The catheter shaft 56 should be bent and cut to expose the inflation conduits 80, 82 respectively The irrigation conduit 84 need not be exposed in this manner, as the manifold 118 includes a substantially straight portion in which the proximal end of the irrigation conduit 84 will reside. As shown in FIG. 9, during the molding process flexible core pins 122, 124 are inserted into the exposed inflation conduits 80, 82 to respectively maintain the openings into the inflation conduits and provide support therefor during the molding process. In a similar manner, a straight core pin 126 is inserted into the irrigation conduit 84, and the catheter 18 is set into the preformed plastic manifold 118. Plastic is then injected into the manifold 118 to form a tight seal, and the core pins 122, 124, 126 are removed after the plastic has hardened.

A variety of means other than cystoscope 20, discussed above, can be provided on the dilation catheter or the sheath for positioning the dilation means relative to an anatomical structure. Typically, the anatomical structures most convenient for positioning the dilation means are the bladder neck and the external sphincter.

Figure 18:
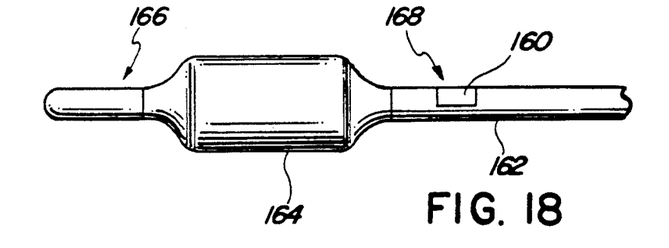
FIG. 18 is an elevational view of a dilation catheter having a transducer thereon for locating an anatomical landmark

For example, referring to FIG. 18, a transducer 160 such as an ultrasound transducer may be molded integrally with or bonded to a dilation catheter 162 having a dilation means 164 thereon. Ultrasound transducer 160 will permit visualization of anatomical structures within the body lumen in accordance with well known instrumentation and techniques. The ultrasound transducer 160 may be positioned either on the distal end 166 of the dilation means 164 (not illustrated), to enable visualization of the bladder neck, or on the proximal end 168 of the dilation means 164, to enable visualization of the external sphincter. The ultrasound transducer may be oriented on the dilation catheter such that the scanned image extends either in a radial plane perpendicular to the axis of the catheter, or in a plane parallel to the axis of the catheter. Alternatively, in an embodiment of the present invention such as that illustrated in FIG. 1, having an introduction sheath 12, an ultrasound transducer 160 can be located at a convenient position on the introduction sheath 12, such as at or near the flexible tip 14.

Electrical wiring from the ultrasound transducer to a conventional external ultrasound monitor may be conveniently run through a lumen in the dilation catheter provided for that purpose, or can be integrally molded within the catheter body. The external display terminal will provide a visual field which enables the clinician to identify the sphincter, the prostate, the bladder or other anatomical features within the urethra. In accordance with the method of the present invention, the non-radiological locating means can also comprise an external ultrasound transducer for observing positioning of the dilation catheter.

Certain anatomical structures within or surrounding the urethra can also be located by means of a detector located on the dilation catheter as discussed in connection with transducer 160, or on an introduction sheath for detecting the muscle contractility or compressive forces in the urethral wall. Thus, muscle contractility, or the presence of muscle in the urethral wall, can be detected by placing a strain gauge, or force or pressure transducer on the catheter shaft in any of the locations discussed in connection with transducer 160. Such a transducer would detect the presence of a radially inwardly directed force, such as would be found at the bladder neck and external sphincter, and would thereby allow positioning of the catheter with the transducer in the region of such radially inwardly directed force. The detector can alternatively be located beneath the deflated balloon or other dilation means. The output from the muscle contractility detector is transmitted by way of wiring extending axially through the catheter or introduction sheath to an external processing device such as are well known in the art.

The contractility detector may be conveniently bonded or molded into the dilation catheter at a position relative to the dilation means such that, when the detector is axially aligned with the external sphincter, the bladder neck, or any other anatomical landmark capable of generating a signal, the dilation means will be disposed within the prostatic urethra. This may be accomplished by providing the muscle contractility detector at a position either distally of, or proximally to, the dilation means as discussed in connection with the location of an ultrasound transducer. Piezoelectric transducers, or other pressure transducers, can be readily adapted for use on a dilation catheter system, as will be appreciated by one of skill in the art. Similarly, a standard EMG pickup for producing an electromylogram can be mounted on the dilation catheter or sheath, and coupled to conventional signal processing equipment. As will be apparent to one of skill in the art, any of the foregoing transducers can be used on a dilation catheter with or without a distal locating balloon such as balloon 60 in FIG. 17.

Optimally, the outer peripheral surface of the transducer will not extent significantly beyond the outer surface of the catheter and, most preferably, the surface of the transducer will be flush-mounted with respect to the immediately surrounding area of the dilation catheter. As will be understood by one of skill in the art, it may be desirable to provide an outer coating or layer of a biocompatible material over the transducer to prevent contact between the transducer and urethral intima, and to minimize any rough or uneven edges.

In accordance with a further embodiment of the present invention, a source of pulsatile pressure (not illustrated) is provided for inflating the dilation balloon. Pumps capable of generating a variable frequency pulsatile pressure are well known in the art, and can readily be constructed by a cam-driven piston pump, as will be appreciated by one of skill in the art. By introducing and withdrawing fluid through the dilation port of the catheter, the balloon can be made to pulse at a desired frequency. Preferably, a pulsatile pressure source is connected to the dilation balloon which is capable of vibration at about the natural body frequency of approximately 8 Hz. High frequency pulsation of the balloon can be accomplished by providing an acoustic transducer on the dilation catheter, such as within the dilation balloon, and driven by an external variable frequency source of acoustic vibration. However, lower or higher frequencies such as from 1/60 Hz to as high as 5000 Hz may also facilitate reduction of the symptoms of obstructive prosthetism.

Figure 19:
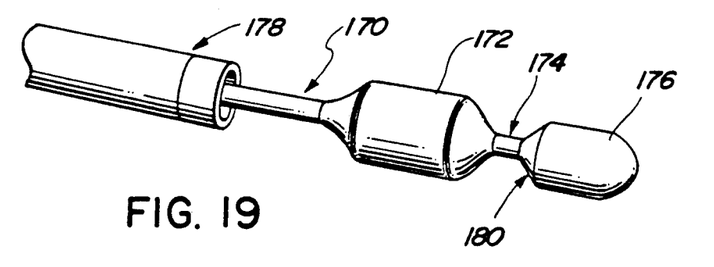
FIG. 19 is a perspective view of a dilation catheter having an integral obturator thereon.

In accordance with a further embodiment of the dilation catheter of the present invention, illustrated in FIG. 19, there is provided a dilation catheter 170, having a dilation balloon 172, or other dilation means thereon, which is provided at its distal end 174 with an integrally molded, or otherwise secured, obturator 176 for facilitating introduction of the dilation catheter within the urethra. The obturator 176 may be molded or formed from any of a variety of materials which are substantially biologically inert in the urethral environment, and which facilitate secure bonding to the material of the dilation catheter shaft 170 so that the obturator 176 will not become detached from the shaft in use. For example, a polyvinylchloride (PVC) obturator may be securely bonded to a PVC catheter shaft.

The dilation catheter 170 having an integral obturator 176 thereon may be used either alone or in combination with an introduction sheath 178, and preferably is used together with an introduction sheath 178. For this purpose, the proximal end 180 of the integral obturator 176 is tapered slightly as illustrated in FIG. 19, so that is may be snugly fitted within the distal end of the introduction sheath 178.

Figure 7:
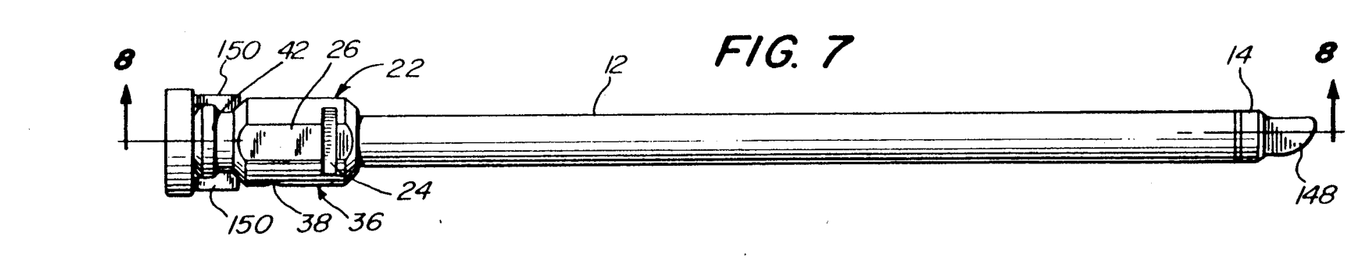
FIG. 7 is a side view of the sheath, having an obturator disposed therein, as ready for insertion into the urethra.
Figure 8:
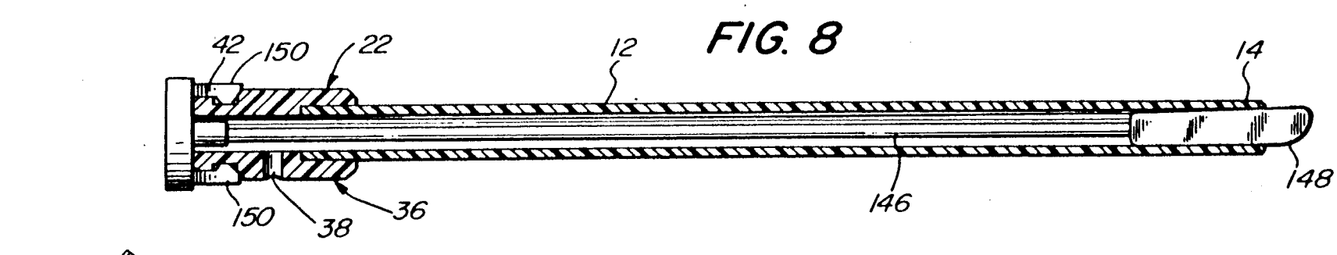
FIG. 8 is a cross-sectional view, taken along line 8—8 of FIG. 7, showing in more detail the obturator removably disposed therein.

An integral obturator 176 can also be configured like the obturator 148 in FIGS. 7 and 8, with a more gradual taper to cooperate with flexible tip 14 of sheath 12. In addition, as with the flexible distal tip 14 illustrated in FIG. 5, sheath 178 can be further provided with a flexible region 179 for receiving proximal end 180 when the catheter is in the retracted position.

Following introduction of the sheath 178 in accordance with the present embodiment of the invention, the dilation catheter 170 and integral obturator 176 may be extended distally relative to sheath 178 to expose the dilation means 172. The dilation means is then positioned in accordance with any of the positioning techniques described herein, and dilation is accomplished. Following dilation, the dilation means is reduced in external diameter, and the dilation catheter is retracted axially into the sheath so that the proximal end 180 of the obturator 176 fits snugly within the distal end of the sheath 178.

Figures 20, 21:
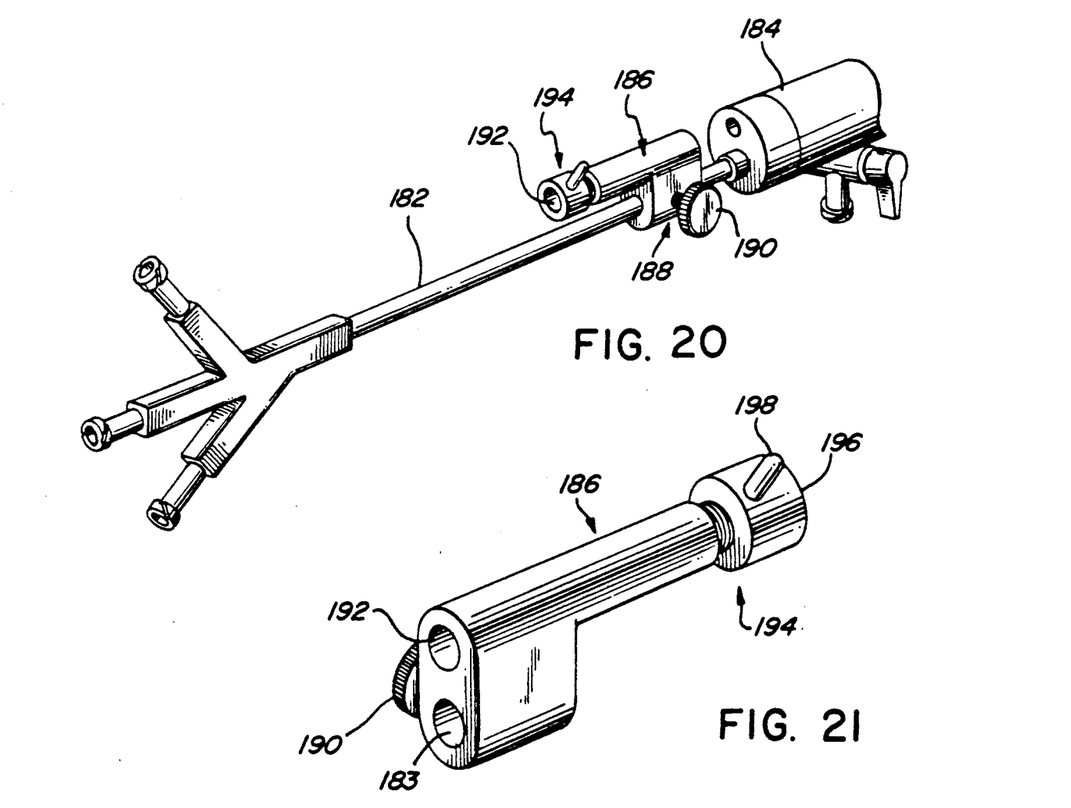
FIG. 20 is a perspective view of a dilation apparatus having a locking bridge.
FIG. 21 is an enlarged perspective view of a locking bridge.

Referring to FIGS. 20 and 21, there is illustrated a locking bridge 186 for facilitating control over the various components of the dilation assembly, according to one embodiment of the present invention. Dilation catheter 182 is illustrated as extending through a dilation assembly housing 184 in a manner similar to that discussed in connection with FIG. 1. Dilation catheter 182 is additionally illustrated as extending through a tubular channel 183 contained in locking bridge 186, enabling a variety of securing functions as will be discussed.

A first locking means 188, such as a thumb screw 190, is provided on the locking bridge 186, for securing the locking bridge 186 with respect to the dilation catheter 182. Although illustrated as a thumb screw 190, the first securing means 188 may comprise any of a variety of means well known to one of skill in the art which may be adapted for securing locking bridge 186 against axial movement along dilation catheter 182.

Locking bridge 186 is further provided with a second tubular channel 192 for receiving a standard cystoscope or other locating means therethrough. Channel 192 is provided with a second securing means 194 for securing the endoscope with respect to locking bridge 186. As discussed in connection with first securing means 188, the second securing means 194 can be any of a variety of means known in the art for securing a tubular member against axial motion through the locking bridge 186.

For example, referring to FIG. 21, the second securing means 194 can comprise a rotatable sleeve 196 having a lever 198 thereon to facilitate rotation. The sleeve 196 is threadably engaged with the body of locking bridge 186, and rotation of sleeve 196 provides a compressive retention force on an elongate body extending through channel 192, such as by compression of an annular ring of elastomeric material, or radial inward movement of a multiple jaw chuck, as are well known in the art. Locking bridge 186 is preferably additionally provided with a further securing means (not illustrated) for securing locking bridge 186 to the dilation assembly housing 184. This further securing means may comprise any of a variety of securing means, as will be appreciated by one of skill in the art.

The foregoing structures enable the clinician to fix the axial position of the dilating means in relation to the sheath, to fix the position of the locating means with respect to the sheath and to alternatively fix the position of the locating means with respect to the dilating means.

METHOD OF USING THE DILATION CATHETER

Figure 15:
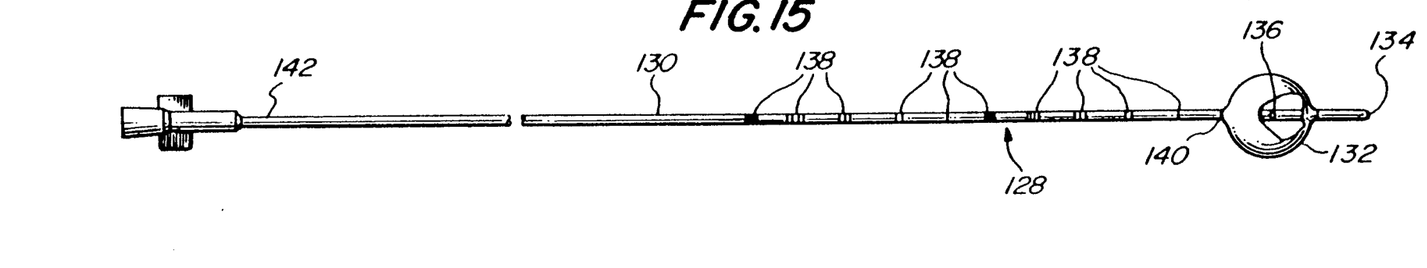
FIG. 15 is a side view of a calibration catheter, showing a partial cut away view of an inflation aperture for the expandable balloon.

Prior to dilating the obstructed urethral lumen, the length of the affected prostatic urethra 68 should be measured. This may be accomplished by the use of a calibration catheter 128, as illustrated in FIG. 15. The calibration catheter 128 is an axially elongate shaft 130, having an expandable balloon 132 located near the distal end 134 thereof, and an inflation conduit (not shown) which extends substantially the entire length of the shaft 130. The expandable balloon 132 is adapted to be inflated through an inflation aperture 136, extending from the inflation conduit by a source of pressurized fluid (not shown). A plurality of graduated markings 138 extend along the exterior shaft 130 of the catheter 128, commencing near the proximal end 140 of the expandable balloon 132, and are adapted to be read from the distal end 134 of the catheter 128 to the proximal end 142.

The calibration catheter 128 is adapted to be received into the sheath of a standard cystoscope, and the cystoscope inserted into the urethra through the penile meatus. Once the distal end 134 and expandable balloon 132 of the calibration catheter 128 enters the bladder 144, the expandable balloon 132 may be inflated, and the catheter 128 slowly withdrawn from the urethra until the balloon 132 becomes lodged within the bladder neck 72. Graduated markings 138, inscribed on the exterior shaft 130 of the catheter 128 can be used to measure the distance between the bladder neck 72 and the lower end 70 of the affected prostatic urethra 68. Once such a measurement has been determined, the expandable balloon 138 may be deflated, and the catheter 128 withdrawn.

An introduction sheath 12, as illustrated in FIGS. 7 and 8 is then readied for insertion through the external urethral opening. An obturator 146, as shown in FIGS. 6, 7 and 8, having a smooth, tapered end 148 with no sharp edges is inserted into the sheath 12, and secured to the hub 42 of the cylindrical housing 22 by chamfered clips 150. The flexible tip 14 of the sheath 12 tapers inwardly, so as to grip the extending portion of the obturator 146 and provide a fairly smooth surface continuation of the introduction sheath. This mild transition between the obturator 146 and sheath 12 is instrumental in reducing damage and trauma to the tender urethral lumen. Once the sheath 12 has been fully inserted within the urethral lumen, the chamfered clips 150 may be released, and the obturator 146 withdrawn.

A catheter shaft 56, having a dilation balloon 62 with a length approximately equivalent to that measured by the calibration catheter 128, is then inserted through one 48 of two boot sleeves of the septum 44, until at least that portion of the catheter shaft 56 to which the expandible balloons 60, 62 are attached extends therethrough. The septum 44 is then friction fit onto the hub 42 of the cylindrical housing 22 such that the catheter 18 is in alignment with the larger diameter ellipsoid section 152 of the sheath 12. The cystoscope lens 20 is then inserted into the other boot sleeve 50, and is then urged through the sheath 12 and into the urethra after placement of the catheter 18.

To provide support for the catheter 18, an elongate stylet 154 may be inserted into the irrigation conduit 84, as illustrated in FIG. 11. The stylet 154 facilitates the ease with which the catheter 18 may be inserted into the urethra, and may remain within the irrigation conduit 84 until the locating balloon 60 is disposed within the bladder 144, at which time the stylet 154 should be removed. Once the locating balloon 60 is within the bladder 144, the inflation conduit 80 may be coupled to a source of pressurized fluid so as to inflate the locating balloon 60. The catheter 18 is then gradually withdrawn from the bladder 144 until the balloon 60 is lodged within the bladder neck 72. When the locating balloon 60 is properly positioned within the neck 72 of the bladder 144, a seal is formed therebetween which prohibits fluids accumulating within the bladder 144 from travelling down the urethra and also prohibits fluids from flowing into and filling up the bladder from the urethra.

Once the catheter 18 has been properly situated with respect to the upper end 72 of the affected prostatic urethra 68, the irrigation conduit 84 may be connected to a source of flushing fluid. The flushing fluid is gravity fed through the irrigation conduit 84 and out the irrigation ports 110, so as to wash existent blood away from the cystoscope lens 20 and provide the urologist with an unobstructed view of the proximal shoulder 64 of the dilation balloon 62, and adjacent organs. Looking through the cystoscope, the urologist can manipulate the catheter 18 to confirm that the dilation balloon 62 is clear of the external urethral sphincter muscle 108, so as to ensure that the sphincter 108 will not inadvertently be dilated.

Upon properly positioning the dilation balloon 62 with respect to both the bladder neck 72 and the sphincter 108, the inflation conduit 82 for the dilation balloon 62 may be connected to a source of pressurized fluid 98. As described above, the inflation source 98 should enable a accurate, progressive dilation under constant control of the pressure being applied within the dilation balloon 62. The device remains within the affected prostatic urethra 68, until sufficient pressure dilation has been achieved. Subsequent to attaining adequate pressure dilation of the prostatic urethra, and eliminating the urinary outflow obstruction, the balloons 60, 62 may be deflated, releasing the pressurized fluid therefrom.

As the dilation balloon 62 is deflated, sharp ridges may form on the outer surface thereof, due to the stiffness of the material from which it was formed. As shown in FIG. 5, the flexible tip 14 of the introduction sheath 12 readily deforms and flares, so as to coerce the dilation balloon 62 back into the sheath 12. When the marking 78, indicative of the time at which the dilation balloon 62 is completely within the sheath 12 becomes visible, the device may be withdrawn from the urethra.

In view of the medical treatment to be administered in using the device of the present invention, it is necessary that the device be aseptically clean. Accordingly, the dilation catheter and sheath can be cleansed and sterilized readily and easily either prior to use thereof, or packaged in this condition, available for immediate use. Further, both the catheter and sheath may be discarded after use, negating the need for recleaning and resterilization.

It will be appreciated that certain structural variations may suggest themselves to those skilled in the art. The foregoing detailed description is to be clearly understood as given by way of illustration, the spirit and scope of this invention being limited solely by the appended claims.

What is claimed is:

1. A method of treating the symptoms of obstructive prostatism by dilation of the prostatic urethra, comprising the steps of:
   inserting a dilation means into the urethra, said dilation means having a non-radiological locating means for positioning the dilation means relative to an anatomical landmark within the urethra which produces a radially inwardly directed force;
   determining the location of the anatomical landmark by detecting the radially inwardly directed force;
   adjusting the location of the dilation means within the urethra with respect to the anatomical landmark; and
   expanding the dilation means so as to radially outwardly dilate the prostatic urethra.

2. An intraluminal dilation apparatus for relieving flow obstructions within a body lumen, comprising:
   an axially elongate dilation catheter adpated for insertion into a body lumen and having a dilation means secured thereto, the catheter being axially movable so as to permit positioning of the dilation means within the obstructed body lumne; and
   a muscle contractility detector, which detects radially inwardly directed forces, positioned relative to the dilation means such that, when the detector is axially aligned with the anatomical landmark, the dilation means is disposed within said body lumen.

3. An intraluminal dilation apparatus as in claim 2, additionally comprising an axially elongate introduction sheath adapted for insertion into the body lumen, wherein the muscle contractility detector is mounted on the sheath.

4. An intraluminal dilation apparatus as in claim 2, wherein the muscle contractility detector is mounted on the dilation catheter.

5. An intraluminal dilation apparatus for relieving flow obsturctions within the urethra, comprising:
   an axially elongate introduction sheath, adapted for insertion into the urethra;
   an axially elongate dilation catheter, ahving a dilation means secured thereto, the catheter extending through and axially movable within said sheath, so as to permit positioning of the dilation means within the urethra;

non-radiological locating means substantially parallel to the sheath for ascertaining the position of said dilating means within the urethra; and an obturator integral with said dilatation catheter for facilitating introduction of the dilating means into the urethra.

6. An intraluminal dilation apparatus for relieving flow obstructions within the urethra, comprising:

an axially elongate introduction sheath, adapted for insertion into the urethra;

an axially elongate dilation catheter, having a dilation means secured thereto, the catheter extending through and axially movable within said sheath, so as to permit positioning of the dilation menas within the obstructed urethra;

non-radiological locating menas substantially parallel to the sheath for ascertaining the position of said dilating means within the urethra;

a locking bridge for facilitating control over the sheath, dilation means and locating means;

a first securing means on the locking bridge for fixing the position of the locating means in relation to the sheath.

7. An intraluminal dilation apparatus as in claim 6, further comrpising a second securing means on the locking bridge for fixing the position of the dilating means relative to the sheath.

8. An intraluminal dilation apparatus as in claim 7, further compising a third securing means on the locking bridge for fixing the position of the locating means relative to the dilating means.

9. An intraluminal dilation apparatus for relieving flow obstructions within a body lumen, comprising:

an axially elongate dilation catheter, having proximal and distal ends and a dilation means secured thereto;

a non-radiological locating means on the catheter for ascertaining the position of the dilating means within the body lumen; and an obturator integrally secured to the distal end of the dilation catheter for facilitating introduction of the dilation catheter into the urethra.

10. A method of treating the symptoms of obstructive prostatism by dilation of the prostatic urethra, comprising the steps of:

inserting a dilation means into the urethra, said dilation means having a tubular support structure disposed thereon and a non-radiological locating means for positioning the dilation means and support structure relative to an anatomical landmark within the urethra;

adjusting the location of the support structure within the urethra with respect to the anatomical landmark using said non-radiological locating means;

expanding the dilation means so as to radially outwardly dilate the prostatic urethra; and removing the dilation means leaving the support structure within the dilated portion of the prostatic urethra.

11. The method of claim 10 wherein said expanding step radially outwardly expands at leat a portion of the support structure.

12. A method of treating the symptoms of obstructive prostatism as in claim 10 wherein the adjusting step is accomplished under direct visualization using an endoscope.

13. An intraluminal dilation apparatus for relieving flow obstructions within the urethra, comprising:

an axially elongate introduction sheath, adapted for insertion into the urethra;

an axially elongate dilation catheter, having a dilation means secured thereto, the catheter extending through and axially movable within said sheath, so as to permit positioning of the dilation means within the obstructed urethra;

non-radiological locating means substantially parallel to the sheath for ascertaining the position of said dilating means within the urethra under direct division; and a locking bridge and means on said locking bridge for limiting axial movement of the dilation means with respect to the non-radiological locating means;

wherein the dilation means is axially movable with respect to the locating means.

14. A method of treating the symptoms of urethral outflow obstructions by dilation of the urethra, comprising the steps of:

inserting a dilation means into the urethra, said dilation means having an axailly elongate support structure disposed thereon and a non-radiological locating means for positioning the dilation means and support structure relative to an anatomica landmark within the urethra;

adjusting the location of the support structure within the urethra wtih respect to the anatomical landmark using said non-radiological locating means;

expanding the dilation means so as to radially outwardly dilate the urethra; and removing the dilation means leaving the support structure within the dilated portion of the urethra.

15. An intraluminal dilation apparatus for restoring patency to a collapsed portion of the urethra, comprising:

an axially elongate dilation catheter adapted for insertion into the urethra and having a dilation means secured thereto, the catheter being axially movable so as to permit positioning of the dilation means within the obstructed urethra;

an axially elongate support structure disposed on said dilation means, the support structure being outwardly radially expandable in response to dilation of the dilation means; and non-radiological locating means substantially parallel to the urethra for ascertaining the position of said dilation means within the urethra under direct vision.

16. A method of treating the symptoms of urethral outflow obstructions by dilation of the urethra, comprising the steps of:

inserting an instrument into the urethra, said instrument having an axially elongate support structure disposed thereon for radially outwardly dilating the urethra;

adjusting the location of the support structure within the urethra with respect to the anatomical landmark using said non-radiological locating means under direct vision;

expanding the support structure so as to radially outwardly dilate the urethra; and removing the instrument, leaving the support structure within the dilated portion of the urethra.

* * * * *

UNITED STATES PATENT AND TRADEMARK OFFICE
CERTIFICATE OF CORRECTION

Page 1 of 2

PATENT NO. : 5,030,227
DATED : July 9, 1991
INVENTOR(S) : Robert F. Rosenbluth, et. al.

It is certified that error appears in the above-indentified patent and that said Letters Patent is hereby corrected as shown below:

Column 14, Line 44, change "adpated" to --adapted--.

Column 14, Line 48, change "lumne" to --lumen--.

Column 14, Line 63, change "obsturctions" to --obstructions--.

Column 14, Line 66, change "ahving" to --having--.

Column 15, Line 16, change "menas" to --means--.

Column 15, Line 18, change "menas" to --means--.

Column 15, Line 22, after "means" insert --and--.

Column 15, Line 27, change "comrpising" to --comprising--.

Column 15, Line 31, change "compising" to --comprising--.

Column 15, Line 45, change "uretha" to --body lumen.--.

Column 15, Line 65, change "leat" to --least--.

Column 16, Line 14, change "division" to --vision--.

Column 16, Line 25, change "axailly" to --axially--.

Column 16, Line 28, change "anatomica" to --anatomical--.

Column 16, Line 31, change "wtih" to --with--.

UNITED STATES PATENT AND TRADEMARK OFFICE
CERTIFICATE OF CORRECTION

PATENT NO. : 5,030,227
DATED : July 9, 1991
INVENTOR(S) : Rosenbluth, et. al.

It is certified that error appears in the above-indentified patent and that said Letters Patent is hereby corrected as shown below:

column 16, line 61, please change "the anatomical landmark" to --an anatomical landmark--.

column 16, line 62, please change "said non-radiological locating means" to --a non-radiological locating means--.

Signed and Sealed this

Eleventh Day of October, 1994

Attest:

BRUCE LEHMAN

Attesting Officer          Commissioner of Patents and Trademarks